(12) United States Patent
Halmann

(10) Patent No.: US 9,649,091 B2
(45) Date of Patent: May 16, 2017

(54) WIRELESS ULTRASOUND IMAGING SYSTEM AND METHOD FOR WIRELESS COMMUNICATION IN AN ULTRASOUND IMAGING SYSTEM

(75) Inventor: Menachem Halmann, Wauwatosa, WI (US)

(73) Assignee: General Electric Company, Schenectady, NY (US)

(*) Notice: Subject to any disclaimer, the term of this patent is extended or adjusted under 35 U.S.C. 154(b) by 1025 days.

(21) Appl. No.: 12/986,361

(22) Filed: Jan. 7, 2011

(65) Prior Publication Data

US 2012/0179037 A1  Jul. 12, 2012

(51) Int. Cl.
*A61B 8/14* (2006.01)
*A61B 8/00* (2006.01)

(52) U.S. Cl.
CPC .......... *A61B 8/4427* (2013.01); *A61B 8/4472* (2013.01); *A61B 8/4477* (2013.01); *A61B 8/54* (2013.01); *A61B 8/585* (2013.01)

(58) Field of Classification Search
None
See application file for complete search history.

(56) References Cited

U.S. PATENT DOCUMENTS

| | | |
|---|---|---|
| 5,964,709 A | 10/1999 | Chiang et al. |
| 6,113,547 A | 9/2000 | Catallo et al. |
| 6,117,085 A | 9/2000 | Picatti et al. |
| 6,139,498 A | 10/2000 | Katsman et al. |
| 6,142,946 A | 11/2000 | Hwang et al. |
| 6,221,020 B1 | 4/2001 | Lysyansky et al. |
| 6,475,146 B1 | 11/2002 | Frelburger et al. |
| 6,526,163 B1 | 2/2003 | Halmann et al. |
| 6,780,154 B2 | 8/2004 | Hunt et al. |
| 7,115,093 B2 | 10/2006 | Halmann et al. |
| 2003/0013966 A1 | 1/2003 | Barnes et al. |
| 2003/0097071 A1 | 5/2003 | Halmann et al. |
| 2004/0015079 A1 | 1/2004 | Berger et al. |
| 2005/0113690 A1 | 5/2005 | Halmann et al. |
| 2005/0124890 A1 | 6/2005 | Halmann et al. |

(Continued)

FOREIGN PATENT DOCUMENTS

| | | |
|---|---|---|
| CN | 201139548 Y | 10/2008 |
| CN | 201398976 Y | 2/2010 |

(Continued)

*Primary Examiner* — Joseph M Santos Rodriguez
(74) *Attorney, Agent, or Firm* — Dean D. Small; The Small Patent Law Group, LLC.

(57) ABSTRACT

A wireless ultrasound imaging system includes plural probes, at least one access point device, and a processing subsystem. Each of the probes has at least one transducer element that is configured to emit ultrasound pulses into one or more imaged bodies and receive echoes of the pulses. The probes are configured to generate ultrasound data based on the echoes and to wirelessly transmit the ultrasound data. The access point device is configured to wirelessly receive the ultrasound data from the probes. The processing subsystem is communicatively coupled with the at least one access point device. The processing subsystem receives the ultrasound data from the probes and creates one or more images based on the ultrasound data. In one aspect, a plurality of the probes is configured to concurrently acquire the ultrasound data.

19 Claims, 9 Drawing Sheets

(56) References Cited

U.S. PATENT DOCUMENTS

| | | | |
|---|---|---|---|
| 2005/0265267 A1* | 12/2005 | Hwang | G06F 19/321 370/310 |
| 2007/0161904 A1 | 7/2007 | Urbano | |
| 2008/0108899 A1 | 5/2008 | Halmann et al. | |
| 2008/0110261 A1 | 5/2008 | Randall et al. | |
| 2008/0110263 A1 | 5/2008 | Klessel et al. | |
| 2008/0110266 A1 | 5/2008 | Randall et al. | |
| 2008/0112265 A1 | 5/2008 | Urbano et al. | |
| 2008/0114239 A1 | 5/2008 | Randall et al. | |
| 2008/0114241 A1 | 5/2008 | Randall et al. | |
| 2008/0114245 A1 | 5/2008 | Randall et al. | |
| 2008/0114246 A1 | 5/2008 | Randall et al. | |
| 2008/0114247 A1 | 5/2008 | Urbano et al. | |
| 2008/0114248 A1 | 5/2008 | Urbano et al. | |
| 2008/0114249 A1 | 5/2008 | Randall et al. | |
| 2008/0114250 A1 | 5/2008 | Urbano et al. | |
| 2008/0114251 A1 | 5/2008 | Weymer et al. | |
| 2008/0114252 A1 | 5/2008 | Randall et al. | |
| 2008/0114253 A1 | 5/2008 | Randall et al. | |
| 2008/0114255 A1 | 5/2008 | Schwartz et al. | |
| 2008/0194960 A1 | 8/2008 | Randall | |
| 2008/0194961 A1 | 8/2008 | Randall | |
| 2008/0194962 A1 | 8/2008 | Randall | |
| 2008/0194963 A1 | 8/2008 | Randall | |
| 2008/0208061 A1 | 8/2008 | Halmann | |
| 2008/0229835 A1 | 9/2008 | Davidsen et al. | |
| 2008/0255451 A1 | 10/2008 | Cohen et al. | |
| 2009/0036778 A1 | 2/2009 | Cohen et al. | |
| 2009/0054768 A1 | 2/2009 | Halmann et al. | |
| 2009/0112099 A1 | 4/2009 | Kurokawa | |
| 2009/0187105 A1* | 7/2009 | Ichikawa | 600/444 |
| 2010/0010348 A1 | 1/2010 | Halmann | |
| 2010/0063398 A1 | 3/2010 | Halmann et al. | |
| 2010/0160783 A1 | 6/2010 | Halmann et al. | |
| 2010/0268503 A1* | 10/2010 | Specht et al. | 702/104 |
| 2010/0312114 A1 | 12/2010 | Karasawa | |

FOREIGN PATENT DOCUMENTS

| | | |
|---|---|---|
| CN | 101677807 A | 3/2010 |
| CN | 101700187 A | 5/2010 |
| JP | 2007538337 | 8/2009 |

* cited by examiner

WIRELESS ULTRASOUND IMAGING SYSTEM AND METHOD FOR WIRELESS COMMUNICATION IN AN ULTRASOUND IMAGING SYSTEM

BACKGROUND OF THE INVENTION

The subject matter described herein relates generally to imaging systems, and more particularly, to ultrasound imaging systems.

Ultrasound imaging systems are used in different applications to image different regions or areas (e.g., different organs) of patients or other objects. For example, an ultrasound imaging system may be utilized to generate images of organs, vasculature, heart or other portions of the body. The ultrasound imaging systems can include cables that mechanically and electrically connect ultrasound probes with the systems. The probes emit ultrasound pulses that back-scatter off of objects within the patient or object being imaged and may return to the probes as echoes. The echoes are converted into ultrasound data that is processed to form an image.

Some known ultrasound imaging systems are limited in the number of probes that can be coupled with the system. For example, the number of ports in the system that are shaped to receive or mate with the cables connected to the probes may be limited, such as to four probes or less. Moreover, many of these systems permit only a single ultrasound probe to be connected to the system by a cable to acquire ultrasound data at a time. The number of cables that may be coupled to the system may be limited. As a result, the amount of ultrasound data and/or the number of patients or objects that can be imaged at a given time by these systems can be limited.

Additionally, the cables that are used in these known imaging systems can be relatively stiff and inflexible. Repeated use of the probes by operators can result in repetitive stress injuries to the operators.

BRIEF DESCRIPTION OF THE INVENTION

In accordance with one embodiment, a wireless ultrasound imaging system is provided. The system includes plural probes, at least one access point device, and a processing subsystem. Each of the probes has at least one transducer element that is configured to emit ultrasound pulses into one or more imaged bodies and receive echoes of the pulses. The probes are configured to generate ultrasound data based on the echoes and to wirelessly transmit the ultrasound data. The access point device is configured to wirelessly receive the ultrasound data from the probes. The processing subsystem is communicatively coupled with the at least one access point device. The processing subsystem receives the ultrasound data from the probes and creates one or more images based on the ultrasound data. In one aspect, a plurality of the probes is configured to concurrently acquire the ultrasound data.

In another embodiment, a method for wireless communication in an ultrasound imaging system is provided. The method includes directing plural probes to acquire ultrasound data by emitting ultrasound pulses into one or more imaged bodies and receive echoes of the pulses and directing the probes to wirelessly transmit the ultrasound data. The method also includes wirelessly receiving the ultrasound data from the probes at one or more access point devices and processing the ultrasound data at an ultrasound processing subsystem that is communicatively coupled with the one or more access point devices to form one or more images. In one aspect, directing the probes to concurrently acquire the ultrasound data includes allocating different acquisition time periods among a plurality of the probes and directing the probes to emit the ultrasound pulses into the body during the acquisition time periods allocated to the probes.

In another embodiment, a computer readable storage medium for a wireless ultrasound imaging system having a processor and plural probes configured to generate ultrasound data by emitting ultrasound pulses into one or more imaged bodies and receiving echoes of the pulses is provided. The computer readable storage medium includes instructions to command the processor to direct a plurality of the probes to acquire the ultrasound data and to direct the probes to wirelessly transmit the ultrasound data. The instructions also command the processor to direct the probes to wirelessly receive the ultrasound data from the probes at one or more access point devices. The instructions command the processor to direct the imaging system to process the ultrasound data at an ultrasound processing subsystem that is communicatively coupled with the one or more access point devices to form one or more images.

DETAILED DESCRIPTION OF THE INVENTION

Figure 1:
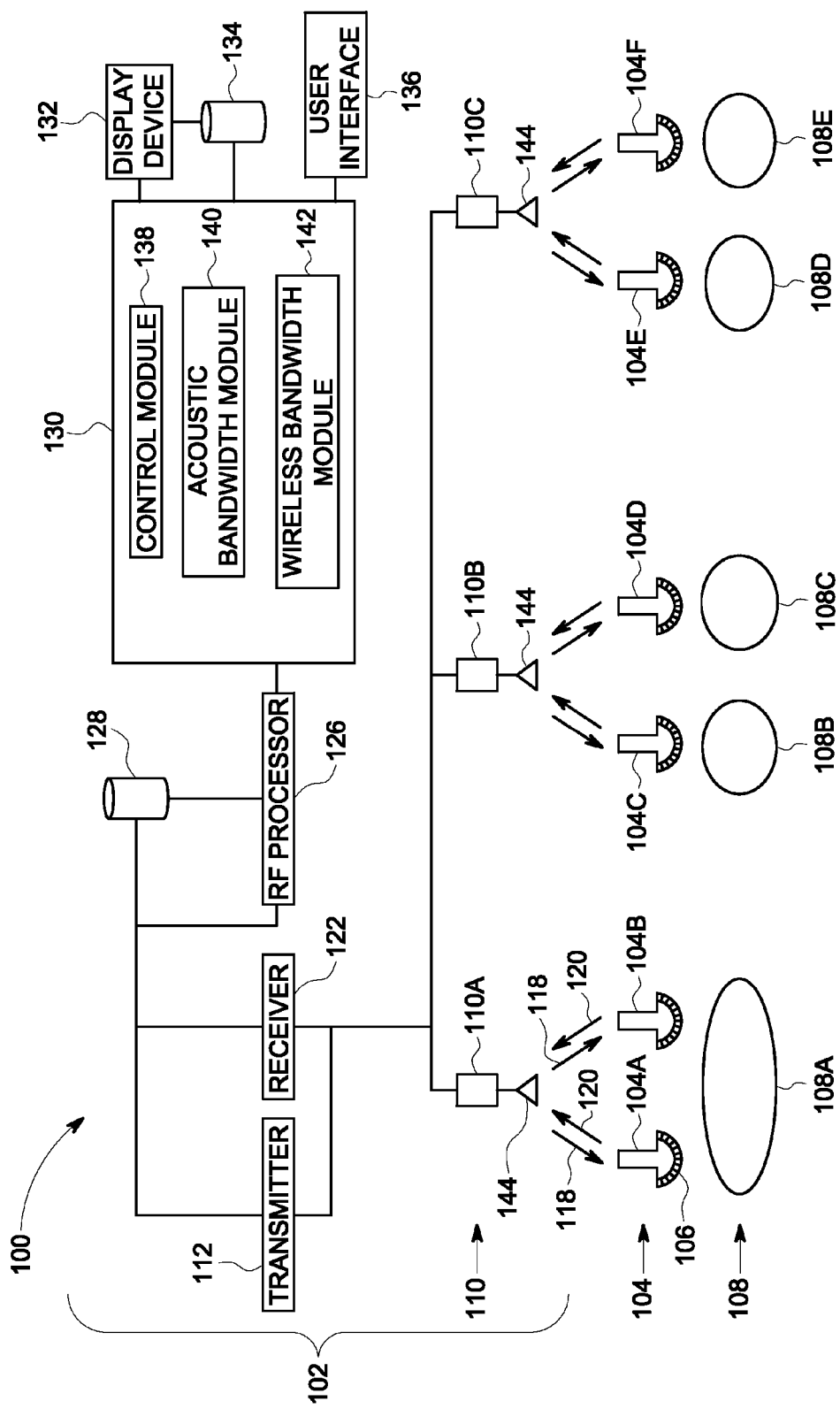
FIG. 1 is a block diagram of one embodiment of a wireless ultrasound imaging system.

The foregoing summary, as well as the following detailed description of certain embodiments of the present invention, will be better understood when read in conjunction with the appended drawings. To the extent that the figures illustrate diagrams of the functional blocks of various embodiments, the functional blocks are not necessarily indicative of the division between hardware circuitry. One or more of the functional blocks (e.g., processors or memories) may be implemented in a single piece of hardware (e.g., a general purpose signal processor or random access memory, hard disk, or the like) or multiple pieces of hardware. Similarly, the programs may be stand alone programs, may be incorporated as subroutines in an operating system, may be functions in an installed software package, and the like. It should be understood that the various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

At least one technical effect of the various embodiments of the systems and methods described herein is to provide for the concurrent (e.g., overlapping time periods with different start and/or end points in time) or simultaneous (e.g., overlapping time periods with the same start and end points in time) acquisition of ultrasound data from one or more imaged bodies by plural ultrasound probes. For example, a single imaging system may have multiple ultrasound probes that acquire ultrasound data from the same patient or from different patients at the same time. The probes can wirelessly transmit the acquired ultrasound data to the imaging system. The imaging system can then generate one or more images based on the acquired ultrasound data.

FIG. 1 is a block diagram of one embodiment of a wireless ultrasound imaging system 100. The system 100 is capable of steering (mechanically and/or electronically) a soundbeam in 3D space, and is configurable to acquire information corresponding to a plurality of two-dimensional (2D) or three-dimensional (3D) representations or images of a region of interest (ROI) in a subject or patient. The ultrasound imaging system 100 may be configurable to acquire 2D and 3D images in one or more planes of orientation. In operation, real-time ultrasound imaging using one or more matrix or 3D ultrasound probes may be provided.

The system 100 includes a processing subsystem 102 that wirelessly communicates with one or more ultrasound probes 104. The probes 104 are generally referred to by the reference number 104 and individually referred to by reference numbers 104a-f, as shown in FIG. 1. While six probes 104 are shown in the illustrated embodiment, alternatively a smaller or greater number of probes 104 may be provided. The probes 104 include one or more transducer elements 106 (e.g., piezoelectric elements) that emit ultrasound pulses into imaged bodies 108 (e.g., a human or non-human patient, a region of interest inside the patient, or an organ or other tissue of the patient). Moreover, while the probes 104 are shown as having the same geometry or shape, alternatively one or more of the probes 104 may have a different geometry, size, and/or shape from one or more other probes 104. Thus, a plurality of different probe types may be used.

The bodies 108 are generally referred to by the reference number 108 and individually referred to by reference numbers 108a-e, as shown in FIG. 1. While five bodies 108 are shown in the illustrated embodiment, alternatively a smaller or greater number of bodies 108 may be imaged by the system 100. The ultrasound pulses may reflect off of one or more structures within the bodies 108 and be reflected back to the probes 104 as echoes. The echoes are received by the transducer elements 106 and converted to electric signals based on, among other things, the intensity of the received echoes. The electric signals represent ultrasound data.

The ultrasound data is wirelessly transmitted to the processing subsystem 102 by the probes 104. For example, the probes 104 may not be conductively coupled with the processing subsystem 102 by data busses, cables, wires, and the like. The probes 104 can communicate the acquired ultrasound data to the processing subsystem 102 in a wireless manner. The processing subsystem 102 processes the ultrasound data to form one or more images of the bodies 108a-e. In one embodiment, multiple probes 104 may concurrently or simultaneously acquire ultrasound data. For example, two or more probes 104 can acquire ultrasound data of the same or different bodies 108 during overlapping time periods, or time periods that at least partially occur during the same time.

The processing subsystem 102 wirelessly communicates with the probes 104 using one or more wireless access point devices 110. The access point devices 110 are generally referred to by the reference number 110 and individually referred to by the reference numbers 110a-c, as shown in FIG. 1. While three access point devices 110 are shown in FIG. 1, alternatively a smaller or greater number of access point devices 110 can be provided. The access point devices 110 provide wireless interfaces between the processing subsystem 102 and the probes 104. The access point devices 110 include antennas 144 that transmit data to the probes 104 and receive data from the probes 104. The access point devices 110 may be mounted inside a room (e.g. an examination room in a hospital or clinic) or disposed within a housing that also holds the circuitry and other hardware of the system 100. The data that is transmitted to the probes 104 through the access point devices 110 may include control instructions, such as transmit beamform instructions that drive the transducer elements 106 to transmit ultrasound pulses. The data that is received by the access point devices 110 from the probes 104 may include ultrasound data, such as data that represents the echoes received by the transducer elements 106 when ultrasound pulses are emitted into the bodies 108.

The processing subsystem 102 includes a processor 130 that performs one or more processing operations according to a plurality of selectable ultrasound modalities. The processor 130 can be provided as a logic based device, such as one or more computer processors or microprocessors. The processor 130 may form the control instructions for the probes 104. A transmitter 112 communicates the control instructions to one or more of the access point devices 110 as wirelessly transmitted control data 118. The access point devices 110 then wirelessly transmit the control instructions to one or more of the probes 104 using the associated antennas 144.

The probes 104 drive the transducer elements 106 to emit ultrasound pulses in accordance with the wirelessly transmitted control data 118. The control data 118 may differ between different probes 104. For example, different probes 104 may receive different control instructions from the transmit beamformer 114 and transmitter 112. The ultrasound pulses may be back-scattered from structures in the imaged bodies 108, such as blood cells or muscular tissue, to produce echoes that return to the transducer elements 106. The transducer elements 106 generate ultrasound data based on the received echoes. As the probes 104a-f may differ from each other and/or different bodies 108a-e may be imaged by the probes 104a-f, the ultrasound data generated by the probes 104a-f may differ from one another. The probes 104 wirelessly transmit the ultrasound data to the access point devices 110 as wireless signals 120.

The wireless signals 120 that represent the ultrasound data are conveyed to a receiver 122. As described below, the probes 104 may include internal processing modules that perform receive beamforming and on the acquired ultrasound data prior to wirelessly communicating the data to the access point devices 110. For example, the processing modules in the probes 104 may delay, apodize and sum each electrical signal that represents ultrasound data with other electrical signals. The summed signals represent echoes from the ultrasound beams or lines. In an alternative embodiment, the processing subsystem 102 may include one or more receive beamformers that performs beamforming operations on the ultrasound data.

In one embodiment, the wirelessly received ultrasound data passes through an RF processor 126. The RF processor 126 may include a complex demodulator (not shown) that demodulates the RF signal to form IQ data pairs representative of the ultrasound data. The RF processor 126 may generate different data types, such as B-mode, color Doppler (velocity/power/variance), tissue Doppler (velocity), and Doppler energy, for one or more scan planes or different scanning patterns. For example, the RF processor 126 may generate tissue Doppler data for multiple (e.g., three) scan planes. The RF processor 126 gathers the information (e.g. I/Q, B-mode, color Doppler, tissue Doppler, and Doppler energy information) related to multiple data slices and stores the data information with time stamp and orientation/rotation information in a computer readable storage medium 128. The information output from the RF Processor 126 and/or the storage medium 128 is referred to herein as the raw ultrasound data. Optionally, the RF signal output from the receive beamformer 124 may be directly routed to the storage medium 128. By way of example, the storage medium may be a tangible and non-transitory memory, such as a computer hard drive, a flash drive, RAM, ROM, an image buffer, or other memory device.

The processor 130 may perform additional or other processing on the acquired ultrasound data. Acquired ultrasound data may be processed and displayed in real-time during a scanning session as the ultrasound data is wirelessly received from the probes 104. Additionally or alternatively, the ultrasound data may be stored temporarily in a computer readable storage medium 134, such as a computer hard drive, flash memory, RAM, ROM, and the like, during a scanning session and then processed and displayed in an off-line operation.

The processor 130 is connected to a user interface 136 that may control operation of the processor 130 and receive user inputs as explained below in more detail. The user interface 136 may include hardware components (e.g., keyboard, mouse, trackball, etc.), software components (e.g., a user display) or a combination thereof. The display device 132 includes one or more monitors that present patient information, including diagnostic ultrasound images to the user for diagnosis and analysis (e.g., images generated using image files having a reduced file size). One or both of the storage media 128 and 134 may store 3D data sets of the ultrasound data, where such 3D data sets are accessed to present 2D (and/or 3D images) as described herein. The images may be modified and the display settings of the display device 132 also manually adjusted using the user interface 136.

While the illustrated embodiment illustrates ultrasound data being acquired by multiple probes 104 to be displayed on a single display device 132 under the control of a single processor 130 and user interface 136, alternatively multiple display devices 132, processors 130, and/or user interfaces 136 may be provided. For example, different subsets or individual probes 104 may be associated with different display devices 132, processors 130, and/or user interfaces 136. Different probes 104 may obtain ultrasound data under the control of different user interfaces 136 and/or processors 130 for processing and display on different display devices 132.

As shown in FIG. 1, the processor 130 may include a control module 138, an acoustic bandwidth module 140, and a wireless bandwidth module 142. One or more of the modules 138, 140, 142 may be sets of instructions stored on a tangible and non-transitory computer readable storage medium (e.g., computer hard drive, flash drive, RAM, or ROM) that direct the processor 130 to perform one or more operations. For example, one or more of the modules 138, 140, 142 may be embodied in a software application.

The control module 138 forms the control instructions for the probes 104. For example, the control module 138 may create control instructions that direct when one or more of the probes 104 are to transmit ultrasound pulses into the bodies 108, when one or more of the probes 104 is to wirelessly transmit acquired ultrasound data to the processing subsystem 102, and/or which of the access point devices 110 one or more of the probes 104 is to wirelessly transmit the acquired ultrasound data. The control module 138 communicates with the acoustic bandwidth module 140 and/or the wireless bandwidth module 142 to determine the instructions that are to be formed and communicated to the probes 104. The control module 138 communicates the control instructions to the access point devices 110, which wirelessly transmit the control instructions to the probes 104 as control data 118. Alternatively, the processing subsystem 102 may include an additional antenna 144 that is not coupled with an access point device 110 to transmit the control instructions to the probes 104 as control data 118.

In operation, multiple probes 104 may acquire ultrasound data for the same processing subsystem 102 at the same time or during overlapping time periods. For example, two or more probes 104 may concurrently acquire ultrasound data from one or more bodies 108 and wirelessly transmit the acquired ultrasound data to the processing subsystem 102 for processing and/or display. Multiple probes 104 may be used to concurrently acquire ultrasound data from the same or different imaged bodies 108. For example, in the illustrated embodiment, plural probes 104a and 104b concurrently acquire ultrasound data representative of the same imaged body 108a. The probes 104a, 104b may acquire ultrasound data from different, non-overlapping regions or volumes of the imaged body 108a, from different, partially overlapping regions or volumes of the imaged body 108a, or from the same region or volume of the imaged body 108a. Other probes 104 may concurrently acquire ultrasound data from different imaged bodies 108. For example, one or more of the probes 104c-f may concurrently acquire ultrasound data from different bodies 108b-e at the same time or during the same time period that one or more other probes 104a-f acquires ultrasound data from one or more of the bodies 108a-e.

Figure 2:
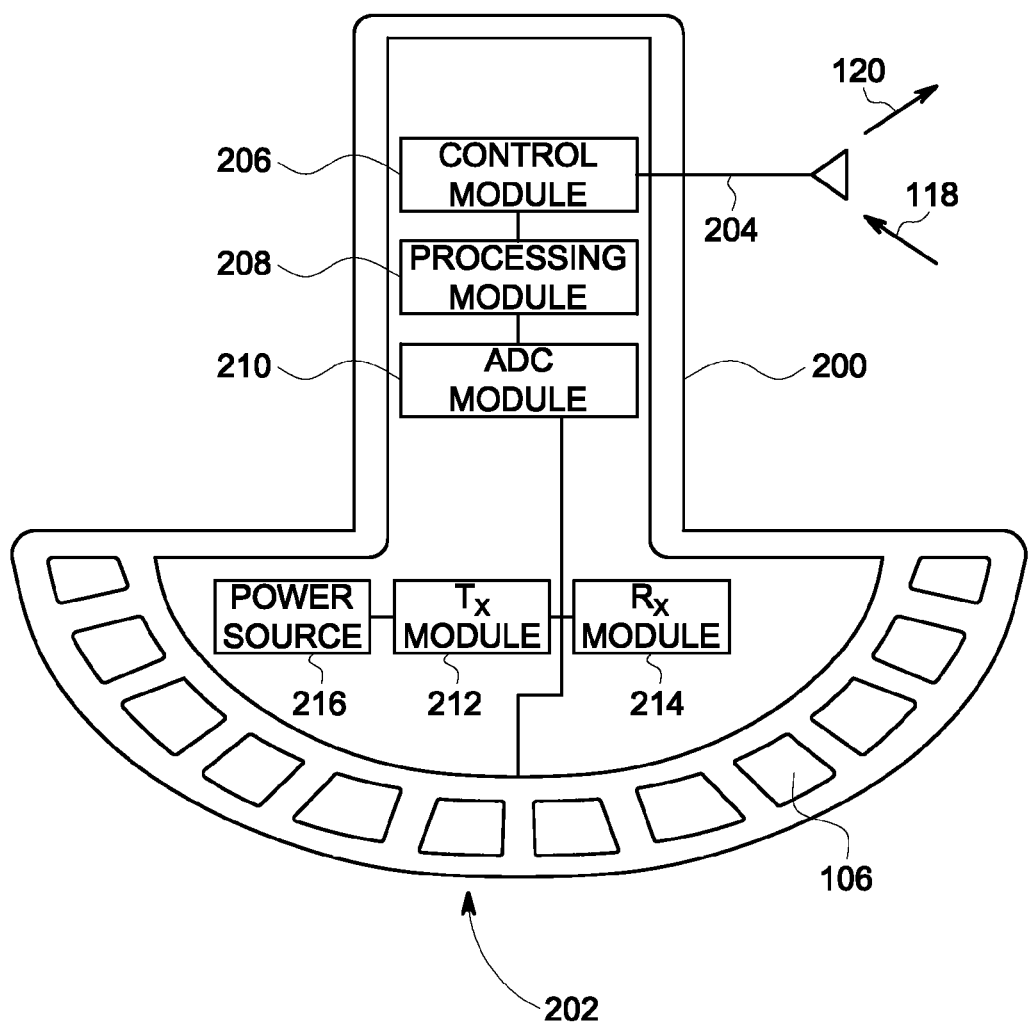
FIG. 2 is a block diagram of one embodiment of an ultrasound probe shown in FIG. 1.

FIG. 2 is a block diagram of one embodiment of the ultrasound probe 104. The probe 104 includes a housing 200 with the transducer elements 106 held by the housing 200 along a transmission face 202 of the housing 200. The transducer elements 106 emit ultrasound pulses from the transmission face 202 and receive ultrasound echoes through the transmission face 202. The transmission face 202 shown in FIG. 2 is a convex surface. Alternatively, the housing 200 and/or the transmission face 202 may have a different shape than the shapes shown in FIG. 2.

The probe 104 includes an antenna 204 for wirelessly communicating data with the processing subsystem 102 (shown in FIG. 1). The position of the antenna 204 shown in FIG. 2 is provided merely as an example. Alternatively, the antenna 204 may be located in another position, such as within the housing 200. The antenna 204 is conductively coupled with a control module 206. The control module 206 may be a logic based device, such as a computer processor, microprocessor, or controller operating based on a set of instructions stored on a computer readable storage medium, such as a software application running on a computer memory. The control module 206 receives control instructions received by the antenna 204 from the processing subsystem 102 (shown in FIG. 1). The control module 206 uses the instructions to control operation of the probe 104. For example, the control module 206 may determine when the probe 104 acquires ultrasound data and/or when the probe 104 wirelessly transmits acquired ultrasound data to the processing subsystem 102.

In one embodiment, the control module 206 is coupled to a processing module 208. The processing module 208 receives digital ultrasound data signals and may process the signals prior to communicating the data to the antenna 204 for wireless transmission to the processing subsystem 102 (shown in FIG. 1). For example, the processing module 208 may compress or filter the data prior to wirelessly communicating the data in order to reduce the total amount of data that is wirelessly transmitted. The processing module 208 may perform transmit and/or receive beamforming operations for the probe 104. For example, the processing module 208 may form transmit beamform instructions that excite, or "drive," the transducer elements 106 of the probe 104 in a timing sequence controlled by the processing module 208. The processing module 208 may perform receive beamform processing on the ultrasound data that is acquired by the transducer elements 106 before wirelessly transmitting the data to the processing subsystem 102. For example, the processing module 208 may delay, apodize and sum each electrical signal that represents ultrasound data with other electrical signals received from the transducer elements 106. The summed signals represent echoes from the ultrasound beams or lines.

The probe 104 includes an analog-to-digital conversion (ADC) module 210 that is coupled with the processing module 208. The ADC module 210 receives ultrasound data in analog form as the data is acquired by the transducer elements 106. For example, the ADC module 210 may receive the analog ultrasound data signals generated by the transducer elements 106 when the transducer elements 106 receive ultrasound echoes. The ADC module 210 converts the analog signals into digital ultrasound data signals prior to communicating the ultrasound data to the processing module 208.

The probe 104 includes an analog front end that includes a transmit module (Tx module) 212 and a receive module (Rx module) 214. The transmit module 212 is controlled by the processing module 208 to drive the transducer elements 106 to emit ultrasound pulses. The receive module 214 receives the analog ultrasound signals generated by the transducer elements 106 and communicates the analog signals to the ADC module 210. The transmit module 212 and the receive module 214 are coupled with the transducer elements 106 and with a power source 216, such as a battery and/or high voltage power source. The power source 216 provides electric energy to power the probe 104. For example, the power source 216 may provide energy to cause the transducer elements 106 to emit ultrasound pulses and/or to power the antenna 204 to transmit the wireless signals 120. In another embodiment, the probe 104 may include a conductive pathway or connector, such as a cable, wire, or other bus extending out of the housing 200 and including a plug or a receptacle for a plug. The conductive pathway and/or connector may be coupled with an external source of power, such as a 120V outlet, to supply power to the probe 104 and/or charge the power source 216. In one embodiment, the conductive pathway and/or connector that is used to supply power to the probe 104 and/or recharge the power source 216 is not used or adapted to communicate data signals, such as control data 118 or ultrasound data.

Returning to the discussion of the imaging system 100 shown in FIG. 1, multiple probes 104 may concurrently acquire ultrasound data from the same or different imaged bodies 108 and wirelessly transmit the acquired ultrasound data to the processing subsystem 102, as described above. In one embodiment, multiple probes 104a, 104b may concurrently image the same body 108a with emitted ultrasound pulses. In order to avoid the ultrasound pulses emitted from one probe 104a or 104b interfering with the ultrasound pulses or received echoes of the other probe 104b or 104a, the processing subsystem 102 may control when one or more of the probes 104a, 104b emits ultrasound pulses into the imaged body 108a. Such control may be referred to as acoustic bandwidth allocation.

In one embodiment, acoustic bandwidth allocation includes dividing the time period over which an imaging procedure is performed on a body 108a into subsets. The time period subsets are assigned to the different probes 104a, 104b that are imaging the body 108a. In one embodiment, each probe 104a, 104b emits ultrasound pulses during the subsets of the time period assigned to the probe 104a or 104b while the other probes 104a or 104b refrain from emitting ultrasound pulses. For example, the probes 104a, 104b may only emit ultrasound pulses during the time period subsets assigned to the respective probes 104a, 104b.

Figure 3:
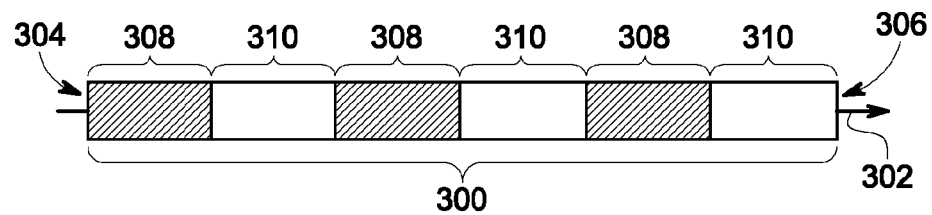
FIG. 3 is an illustration of an ultrasound imaging procedure time period divided into acquisition time periods according to an acoustic bandwidth allocation procedure in accordance with one embodiment.

FIG. 3 is an illustration of an ultrasound imaging procedure time period 300 divided into acquisition time periods according to an acoustic bandwidth allocation procedure in accordance with one embodiment. The time period 300 represents the time window over which an imaging procedure is performed on a body 108a (shown in FIG. 1) by two or more probes 104a, 104b (shown in FIG. 1). The time period 300 is shown along a linear time axis 302 and extends from a beginning time 304 to an ending time 306. The beginning time 304 represents the point in time at which an operator begins the transmission of ultrasound pulses into the body 108a (e.g., a patient or object being ultrasonically imaged) from the probe 104a or 104b. The ending time 306 represents the point in time at which the operator stops the transmission of ultrasound pulses into the body 108a from the probes 104a and/or 104b. The ending time 306 may be a predetermined time, such as a predetermined length of time following the beginning time 304, or may be a point in time that occurs when an operator of the probe 104a or 104b manually terminates the imaging procedure.

The acoustic bandwidth module 140 (shown in FIG. 1) of the processor 130 (shown in FIG. 1) in the processing subsystem 102 (shown in FIG. 1) allocates the time period 300 between the probes 104a, 104b (shown in FIG. 1) that are imaging the same body 108a (shown in FIG. 1) during the same imaging procedure. As shown in FIG. 3, the time period 300 is allocated among the probes 104a, 104b by dividing the time period 300 into several acquisition time periods 308, 310. The acquisition time periods 308 indicate the time periods when the probe 104a acquires ultrasound data from the body 108a (e.g., emits ultrasound pulses into the body 108a) and when the probe 104b does not acquire ultrasound data from the body 108a (e.g., does not emit ultrasound pulses into the body 108a). The acquisition time periods 310 indicate the time periods when the probe 104b acquires ultrasound data from the body 108a and when the probe 104a does not acquire ultrasound data from the body 108a. In the illustrated embodiment, the acquisition time period 300 is allocated among two probes 104a, 104b. Alternatively, the acquisition time period 300 may be evenly or unevenly allocated among three or more probes 104.

The acquisition time periods 308, 310 are non-overlapping sections of the time period 300 in the illustrated embodiment. As a result, the probe 104a that acquires ultrasound data during a preceding acquisition time period 308 stops acquiring ultrasound data when the acquisition time period 308 ends and/or the subsequent acquisition time period 310 begins. Similarly, the probe 104b that acquires ultrasound data during the following acquisition time period 310 begins acquiring ultrasound data when the acquisition time period 308 ends and/or the subsequent acquisition time period 310 begins. The probes 104a, 104b do not acquire ultrasound data at the same time during the same instant in time in the illustrated embodiment. Alternatively, one or more of the sequential acquisition time periods 308, 310 may at least partially overlap each other. For example, the probes 104a, 104b may acquire ultrasound data at the same instants in time by emitting ultrasound pulses into the body 108a at the same time encompassed by the overlapping portions of the acquisition time periods 308, 310.

In one embodiment, the sum total of the acquisition time periods 308 during the time period 300 is equal to or approximately equal to (e.g., within 1%, 5%, or 10%) the sum total of the acquisition time periods 310 of the time period 300. As a result, each of the probes 104a, 104b acquiring ultrasound data during the time period 300 may have an equal or approximately equal amount of time to acquire ultrasound data from the body 108a. Alternatively, one or more of the probes 104 may have priority over one or more other probes 104. For example, if two probes 104 have different priorities attempt to acquire ultrasound data from a common body 108 at the same time, the probe 104 having the higher priority may acquire ultrasound data while the lower priority probe 104 refrains from transmitting ultrasound pulses and/or otherwise acquiring ultrasound data.

Returning to the discussion of the system 100 shown in FIG. 1, in order to allocate the time period 300 (shown in FIG. 3) of an imaging procedure among a plurality of probes 104 imaging a common body 108, the acoustic bandwidth module 140 may identify which of the probes 104 are transmitting ultrasound pulses into the common body 108. In one embodiment, each of the probes 104 is associated with a unique network address. The network addresses of the probes 104a, 104b that are imaging the same body 108a may be input into the processing subsystem 102 and associated with the body 108a. For example, the user interface 136 may be used to manually (e.g. typing or speaking) or automatically (e.g. barcode scanning) input which probes 104a, 104b are to be used in an upcoming imaging procedure and which body 108a will be imaged by the probes 104a, 104b. The body 108a may be associated with a unique identity, such as a patient identification code. The acoustic bandwidth module 140 may associate the identities of the bodies 108 with the unique addresses of the probes 104 used to image the bodies 108. In the illustrated embodiment, the acoustic bandwidth module 140 associates the identity of the body 108a with the addresses of the probes 104a, 104b.

The acoustic bandwidth module 140 may associate additional information related to an imaging procedure with the plural probes 104a, 104b used to image a common body 108a. This additional information may be used in addition to the addresses of the probes 104a, 104b to determine when the different probes 104a, 104b transmit ultrasound pulses into a common body 108a. As one example, this additional information may include frame rates at which the probes 104a, 104b acquire the ultrasound data. The frame rate represents the speed at which a probe 104 transmits ultrasound pulses into a body 108. For example, at a frame rate of 30 Hz, a probe 104 may transmit ultrasound pulses into a body 108, or acquire a frame of ultrasound data, thirty times per second. The probes 104a, 104b may transmit ultrasound pulses at different frame rates and the acoustic bandwidth module 140 may vary or change the time periods during which the different probes 104a, 104b acquire ultrasound data based on the respective frame rates of the probes 104a, 104b.

As another example, the additional information used by the acoustic bandwidth module 140 to determine when the probes 104a, 104b transmit ultrasound pulses includes a type of ultrasound images that are generated based on the ultrasound data acquired by each of the probes 104a, 104b. The type of ultrasound image can represent a category of body part or region of interest in the body 108 that is imaged by the ultrasound pulses or a category of different images. By way of example, different categories of body parts or regions of interest may include the heart, gastrointestinal regions, muscles, tendons, fetuses, and the like. However, other categories may be used. With respect to different categories of images, the categories may include 2D images, 3D images, B-mode, Doppler, echocardiographic images, Focused Assessment with Sonography for Trauma (FAST) images, gastroenterologic images, gynecologic images, carotid ultrasonographic images, obstetrical ultrasound images, transcranial ultrasound images, musculoskeletal images, arterial sonographic images, thrombosonographic images, venosonographic images, and the like. However, other categories of images may be used. The different types and/or categories of images that are obtained by the probes 104 may require different frame or acquisition rates, or different amounts of ultrasound data to form the ultrasound images. The acoustic bandwidth module 140 may vary when the probes 104a, 104b acquire ultrasound data of the body 108a relative to each other based on the type of ultrasound data and/or the categories of images generated by the probes 104a, 104b.

As another example, the additional information used by the acoustic bandwidth module 140 to determine when the probes 104a, 104b transmit ultrasound pulses includes a number of probes 104a, 104b that are concurrently acquiring ultrasound data from a common body 108a, or how many probes 104a, 104b are acquiring ultrasound data from the body 108a during the same time period or within the same time window.

Figure 4:
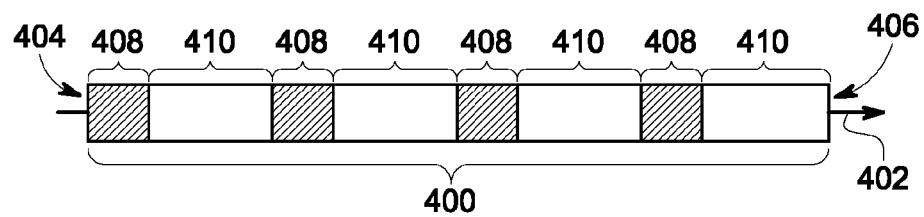
FIG. 4 is an illustration of an ultrasound imaging procedure time period divided into subset time periods according to an acoustic bandwidth allocation procedure in accordance with another embodiment.

FIG. 4 is an illustration of an ultrasound imaging procedure time period 400 divided into subset time periods according to an acoustic bandwidth allocation procedure in accordance with another embodiment. Similar to the time period 300 shown in FIG. 3, the time period 400 represents the time window over which an imaging procedure is performed on a body 108a (shown in FIG. 1) by two or more probes 104a, 104b (shown in FIG. 1). The time period 400 is shown along a linear time axis 402 and extends from a beginning time 404 to an ending time 306.

As shown in FIG. 3, the acoustic bandwidth module 140 may approximately evenly distribute the time period 300 between the probes 104a, 104b such that each acquisition time period 308, 310 of the time period 300 is approximately equal to the other acquisition time periods 308, 310. Alternatively, the acoustic bandwidth module 140 may unevenly distribute or allocate the time period 400 among the probes 104a, 104b into acquisition time periods 408, 410, as shown in FIG. 4. The acquisition time periods 408 are shorter than the acquisition time periods 410, resulting in the probe 104a having shorter acquisition time periods 408 to acquire ultrasound data from the body 108a relative to the acquisition time periods 410 allocated to the probe 104b. In one embodiment, the sum total of time encompassed by all of the acquisition time periods 408 is less than the sum total of time encompassed by all of the acquisition time periods 410 during the time period 400. For example, the probe 104a that acquires ultrasound data during the acquisition time periods 408 may acquire ultrasound data over a smaller total time period than the probe 104b that acquired ultrasound data during the acquisition time periods 410 during the time period 400. Alternatively, there may be an unequal distribution of the acquisition time periods 408, 410 within the time period 400. For example, the acquisition time periods 408, 410 may proceed in the sequence shown in FIG. 4 for a portion of the time period 400 before changing the order and/or duration of one or more of the acquisition time periods 408, 410 for the remainder or another portion of the time period 400.

The duration of one or more of the acquisition time periods 408, 410 and/or the order or sequence of the acquisition time periods 408, 410 may be based or vary on the additional information related to the imaging procedure that is described above. For example, the duration of the acquisition time periods 408, 410 may vary based on the frame rates at which the probes 104a, 104b acquire the ultrasound data. A probe 104a having a higher frame rate may have shorter acquisition time periods 408 relative to a probe 104b having a lower frame rate. For example, the acoustic bandwidth module 140 (shown in FIG. 1) may allocate shorter acquisition time periods 408 of the time period 400 to the probe 104a having a higher frame rate (e.g. 60 Hz) and/or allocate longer acquisition time periods 410 of the time period 400 to the probe 104b having a lower frame rate (e.g. 30 Hz).

As another example, the duration of the acquisition time periods 408, 410 may vary based on the type of ultrasound images that are formed based on the ultrasound data obtained by each of the probes 104a, 104b. For example, some types of ultrasound images (e.g. 3D images) may require more ultrasound data to form the images than other types of ultrasound images (e.g. 2D images). In order to meet the greater data requirements or needs of some types of images, the acoustic bandwidth module 140 may allocate longer acquisition time periods 410 to the probe 104b that is acquiring ultrasound data for the images requiring greater amounts of data and/or allocate shorter acquisition time periods 408 to the probe 104a that is acquiring ultrasound data for the images requiring smaller amounts of data.

In another example, the duration of the acquisition time periods 408, 410 may vary based on the category of body part or region of interest that is imaged by one or more of the probes 104a, 104b. For example, some body parts (e.g. hearts) may require more ultrasound data to form image of the heart than other types of ultrasound images (e.g. obstetrical ultrasound images). In order to image some body parts or regions of interest that require larger amounts of data, the acoustic bandwidth module 140 may allocate longer acquisition time periods 410 to the probe 104b that is acquiring ultrasound data for the body parts or regions requiring more ultrasound data to image the body parts or regions and/or allocate shorter acquisition time periods 408 to the probe 104a that is acquiring ultrasound data for other body parts or regions.

As another example, the acoustic bandwidth module 140 may allocate the length of the acquisition time periods 408, 410 based on the number of probes 104a, 104b that are imaging a common body 108a. For example, in order to keep the total time period 400 of an imaging procedure of within reason or within predetermined time limits, the acoustic bandwidth module 140 may shorten one or more of the acquisition time periods 408, 410 (or 308, 310) in order to accommodate imaging of the body 108a by multiple probes 104a, 104b.

Returning to the discussion of the imaging system 100 shown in FIG. 1, multiple probes 104 may concurrently acquire ultrasound data from the imaged bodies 108 and wirelessly transmit the acquired ultrasound data to the processing subsystem 102, as described above. The access point devices 110 and the probes 104 may form nodes of a wireless network. With wireless networks, the concurrent or simultaneous transmission of data to one or more common access points may result in interference or degradation of the wirelessly transmitted data. In some cases, one or more packets or segments of the wirelessly transmitted data may be lost (e.g., not be received by an access point). In order to reduce the interference between wirelessly transmitted data from the probes 104 to the access point device 110, the processing subsystem 102 may control when the probes 104 wirelessly transmit acquired ultrasound data to the access point devices 110. Such control may be referred to as wireless bandwidth allocation.

In one embodiment, wireless bandwidth allocation includes assigning different time periods to different probes 104. The time periods are assigned to the different probes 104a-f that are transmitting acquired ultrasound data to the access point devices 110. Each probe 104 may transmit acquired ultrasound data (or a portion of the ultrasound data acquired by the probe 104) during the time period assigned to the probe 104 while the one or more other probes 104 do not wirelessly transmit acquired ultrasound data. For example, the probes 104 may only wirelessly transmit acquired ultrasound data to the access point devices 110 during the time periods assigned to the respective probes 104. The time periods that are assigned to the probes 104 for wirelessly transmitting acquired ultrasound data may be referred to as transmission time periods.

Figure 5:
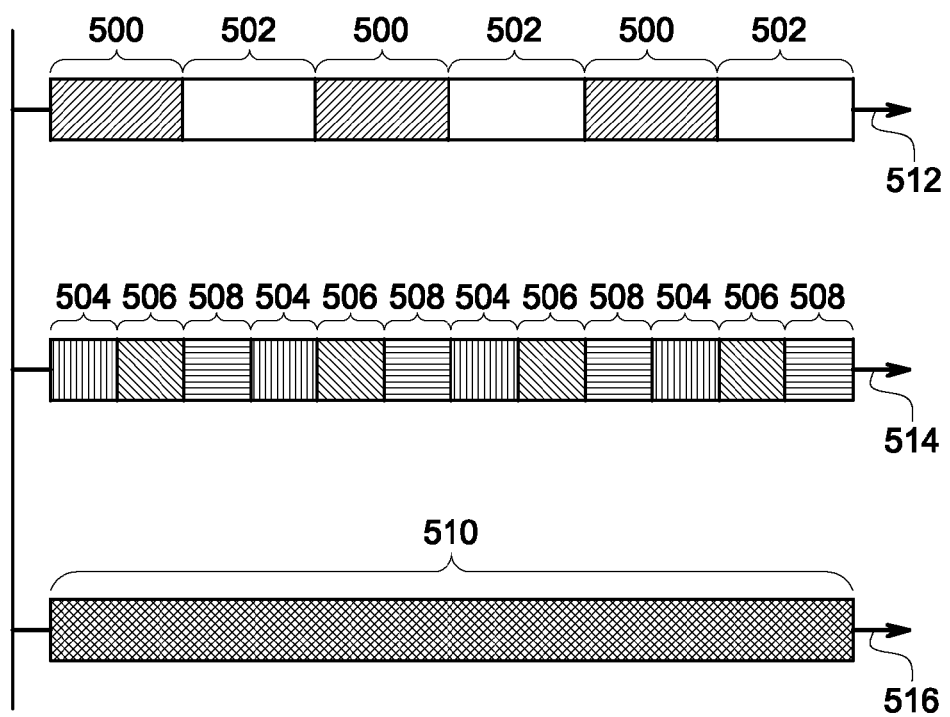
FIG. 5 is an illustration of one embodiment of several transmission time periods assigned to different probes shown in FIG. 1.

FIG. 5 is an illustration of one embodiment of several transmission time periods 500, 502, 504, 506, 508, 510 assigned to different probes 104 shown in FIG. 1. The transmission time periods are assigned or allocated to the probes 104 in order to avoid significant interference between wirelessly transmitted ultrasound data from the probes 104 to the access point devices 110 (shown in FIG. 1). For example, the transmission time periods are assigned to reduce dropped packets of ultrasound data or other lost or corrupted ultrasound data.

The transmission time periods are shown along several horizontal axes 512, 514, 516. The horizontal axes 512, 514, 516 represent time, with each of the transmission time periods shown overlying one of the horizontal axes to indicate the span of time over which ultrasound data is transmitted by a probe 104 assigned to the various transmission time periods. The wireless bandwidth module 142 (shown in FIG. 1) of the processor 130 (shown in FIG. 1) in the processing subsystem 102 (shown in FIG. 1) allocates or assigns the transmission time periods among the probes 104 (shown in FIG. 1) that are concurrently acquiring ultrasound image data.

The different horizontal axes 512, 514, 516 may be associated with different access point devices 110 (shown in FIG. 1). For example, the top horizontal axis 512 may be associated with the access point device 110a, the middle horizontal axis 514 may be associated with the access point device 110b, and the bottom horizontal axis 516 may be associated with the access point device 110c. The transmission time periods are shown on different axes 512, 514, 516 to indicate when each access point device 110 wirelessly receives the ultrasound data acquired by the various probes 104. For example, the access point devices 110 may be assigned unique addresses in the wireless network. The probes 104 may each wirelessly transmit the ultrasound data acquired by the probe 104 to one of the unique addresses of the access point devices 110. The unique address of an access point device 110 may be assigned to the probe 104. For example, one or more probes 104 may be associated with an access point device 110 based on the proximity of the probes 104 to the access point device 110, the number of probes 104 assigned to the access point device 110, the number of probes 104 assigned to other access point devices 110, the number of probes 110 and/or access point devices 110 in the wireless network, and the like. The probes 104 may transmit the acquired ultrasound data to a particular access point device 110 by transmitting the ultrasound data as network data, such as by transmitting the data in packets having an address in a header field of the packet. The address in the header field may match the address of the access point device 110 that is to receive the ultrasound data.

With respect to the embodiment shown in FIG. 5, if the horizontal axis 512 is associated with the access point device 110a (shown in FIG. 1) and the probes 104a and 104b (shown in FIG. 1) are transmitting the ultrasound data to the access point device 110a, then the wireless bandwidth module 142 (shown in FIG. 1) may direct the probes 104a, 104b (via the control data 118 shown in FIG. 1) to transmit to the access point device 110a. The wireless bandwidth module 142 may allocate the time periods 500, 502 between the probes 104a, 104b such that only one of the probes 104a, 104b is transmitting to the access point device 110a at a given time. For example, the probe 104a may transmit data during the time periods 500 and the probe 104b may transmit data during the time periods 502. Alternatively, the wireless bandwidth module 142 may allocate the time periods between the probes assigned to an access point device such that more than two probes concurrently or simultaneously transmit ultrasound data to the same access point device.

If the horizontal axis 514 is associated with the access point device 110b (shown in FIG. 1) and the probes 104c, 104d, and 104e (shown in FIG. 1) are transmitting the ultrasound data to the access point device 110b, then the wireless bandwidth module 142 (shown in FIG. 1) may direct the probes 104c, 104d, 104e to transmit acquired ultrasound data to the access point device 110b. For example, the probe 104c may transmit data to the access point device 110b during the time periods 504, the probe 104d may transmit data to the access point device 110b during the time periods 506, and the probe 104e may transmit data to the access point device 110b during the time periods 508. As shown in FIG. 5, the time periods 504, 506, 508 proceed in a round-robin sequence, or a sequence that evenly proceeds through the probes 104c, 104d, 104e assigned to the same access point device 110b with each probe 104c, 104d, 104e having the same or approximately the same total time to transmit to the access point device 110b. Alternatively, the time periods 504, 506, 508 may proceed in another order, such as an order that provides more time periods to one of the probes relative to other probes, a random order, or another non-round robin order.

If the horizontal axis 516 is associated with the access point device 110c (shown in FIG. 1) and the probe 104f is transmitting ultrasound data to the access point device 110c, then the wireless bandwidth module 142 (shown in FIG. 1) may direct the probe 104f to transmit acquired ultrasound data to the access point device 110f. For example, the probe 104f may be the only probe 104 that is directed to transmit data to the access point device 110c during the time shown in FIG. 5 along the horizontal axis 516. As a result, the probe 104f transmits data during the time period 510 without alternating time periods with other probes 104.

Alternatively, one or more of the horizontal axes 512, 514, 516 may represent different channels of one or more access point devices 110 (shown in FIG. 1). In one embodiment, multiple probes 104 (shown in FIG. 1) may wirelessly transmit to a single access point device 110, with the probes 104 using different channels and different transmission time periods. The channels may represent different frequencies at which ultrasound data is transmitted to the access point device 110. The probes 104 may be assigned different channels of the access point device 110 by the wireless bandwidth module 142 (shown in FIG. 1), such as by transmitting the assigned channel to the probes 104 as control data 118 (shown in FIG. 1). The probes 104 wirelessly transmit acquired ultrasound data to the access point device 110 during the transmission time periods allocated to the various probes 104 on the channels assigned to the various probes 104 in one embodiment.

In another embodiment, one or more of the probes 104 (shown in FIG. 1) may not be assigned or logically connected with an access point device 110 (shown in FIG. 1). For example, one or more of the probes 104 may not be assigned to an access point device 110 such that the probe 104 transmits ultrasound data that is addressed to the access point device 110. Instead, the probe 104 may wirelessly transmit the ultrasound data in a broadcast manner such that one or more access point devices 110 may receive the broadcast ultrasound data. The probe 104 may be allocated transmission time periods from the wireless bandwidth module 142 (shown in FIG. 1), as described above, based on the number of probes 104 that are broadcasting ultrasound data. The ultrasound data may be broadcast in packets or other network data forms having identifying information that indicates which probe 104 transmitted the data. The control module 138 (shown in FIG. 1) and/or the receive beamformer 124 (shown in FIG. 1) may use the identifying information to associate the various wirelessly receive ultrasound data packets with the different probes 104 that acquired the data.

During a time period when a probe 104 (shown in FIG. 1) is not transmitting ultrasound data to an access point device 110 (shown in FIG. 1), the probe 104 may continue to acquire ultrasound data from a body 108 (shown in FIG. 1). For example, if the probe 104a wirelessly transmits ultrasound data to the access point device 110a during the time period 500 but does not transmit ultrasound data during the time period 502, the probe 104a may continue to acquire ultrasound data from the body 108a during the time period 502. As a result, the time periods when a probe 104 acquired ultrasound data (which may be determined by the acoustic bandwidth module 140 shown in FIG. 1) may not coincide with the time periods when the probe 104 wirelessly transmits the acquired ultrasound data to an access point device 110 (which may be determined by the wireless bandwidth module 142 shown in FIG. 1). Alternatively, the acquisition time periods (e.g., the time periods allocated to the probe 104 to acquire ultrasound data) may coincide with the transmission time periods (e.g., the time periods allocated to the probe 104 for wirelessly transmitting the acquired ultrasound data to an access point device 110). By "coincide," it is meant that an acquisition time period and a transmission time period have the same beginning and ending points in time and last for the same amount of time. Two time periods may not coincide when the time periods have different beginning points in time, different ending points in time, and/or last different amounts of time.

In another embodiment, the acquisition time periods and the transmission time periods may not coincide, but may at least partially overlap each other. For example, a probe 104 (shown in FIG. 1) may acquire ultrasound data and not wirelessly transmit the acquired ultrasound data for a first portion of an acquisition time period that does not overlap a transmission time period; acquire and wirelessly transmit ultrasound data to an access point device 110 (shown in FIG. 1) during a second period of an acquisition time period that overlaps a transmission time period; and wirelessly transmit but not acquire ultrasound data during a third time period that occurs after the acquisition time period but during a transmission time period.

The probe 104 (shown in FIG. 1) may acquire ultrasound data and store the acquired ultrasound data in the memory 212 (shown in FIG. 2) before wirelessly transmitting the ultrasound data to an access point device 110 (shown in FIG. 1). For example, if the acquisition and transmission time periods of the probe 104 do not coincide, such as the transmission time period trailing or occurring after the acquisition time period of the probe 104, then the probe 104 may acquire ultrasound data and at least temporarily store the ultrasound data in the memory 212. The memory 212 may serve as a cache to temporarily hold the ultrasound data until the next transmission time period, or the next transmission time period that is available to transmit the ultrasound data.

In one embodiment, the user interface 136 may accept manual input from an operator of one or more of the probes 104 and/or the system 100 to manually adjust the acoustic and/or wireless bandwidth allocated to one or more of the probes 104. For example, an operator may use a keyboard, stylus, touchscreen, microphone, button, toggle, dial, or other input device of the user interface 136 to increase or decrease the length and/or frequency of acquisition time periods that are allocated to one or more of the probes 104 relative to one or more other probes 104. Alternatively or in addition to manually changing the acquisition time periods, an operator may use the user interface 136 change the length and/or frequency of transmission time periods that are allocated to one or more of the probes 104 relative to one or more other probes 104. The operator may change the acquisition and/or transmission time periods for one or more probes 104 in order to increase the frame rate and/or resolution of those probes 104. The allocation of the acquisition and/or transmission time periods may return to the previous lengths and/or frequencies after a predetermined time periods expires, or after additional manual input is received from the operator.

Figure 6A:
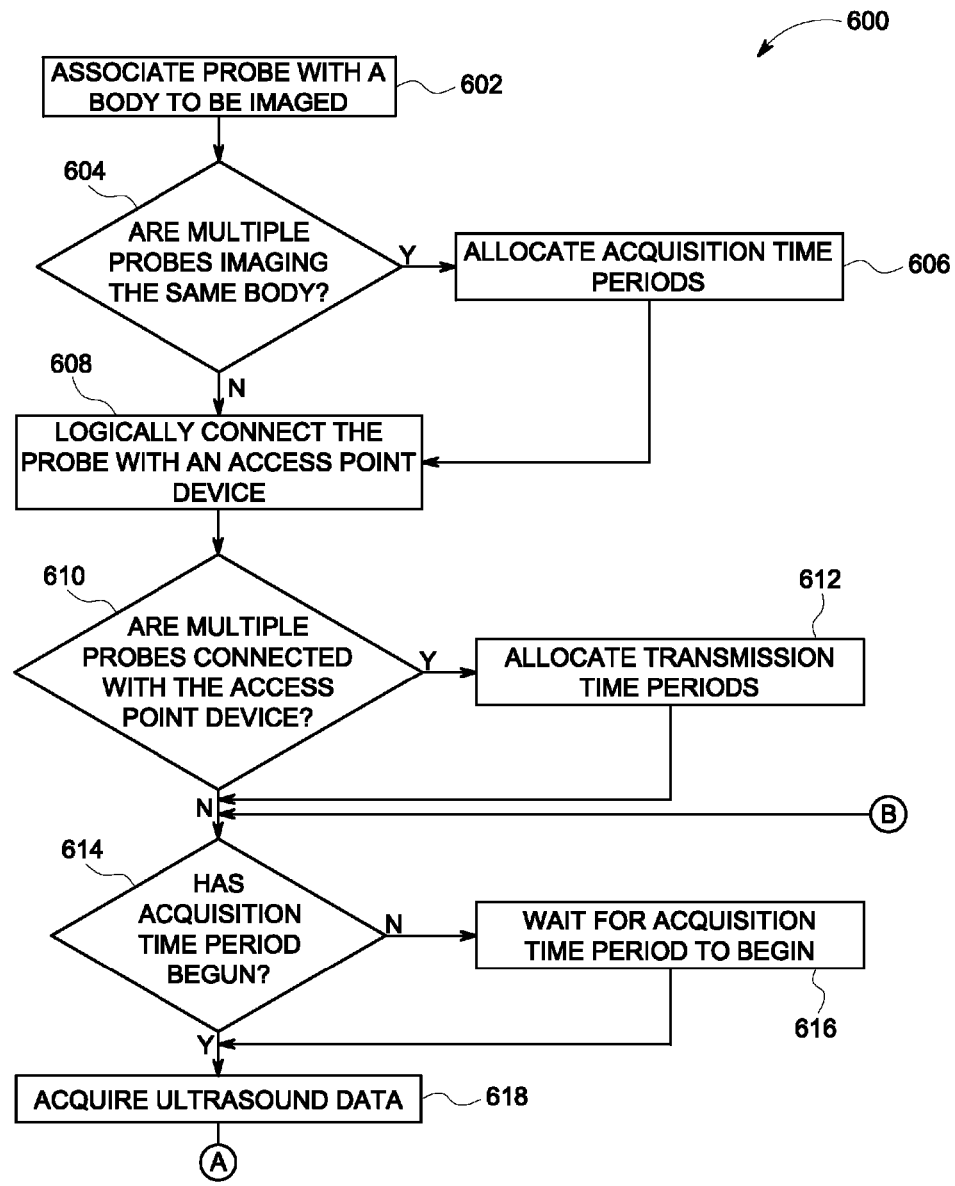
FIGS. 6A and 6B are a flowchart of one embodiment of a method for wireless communication in an ultrasound imaging system.
Figure 6B:
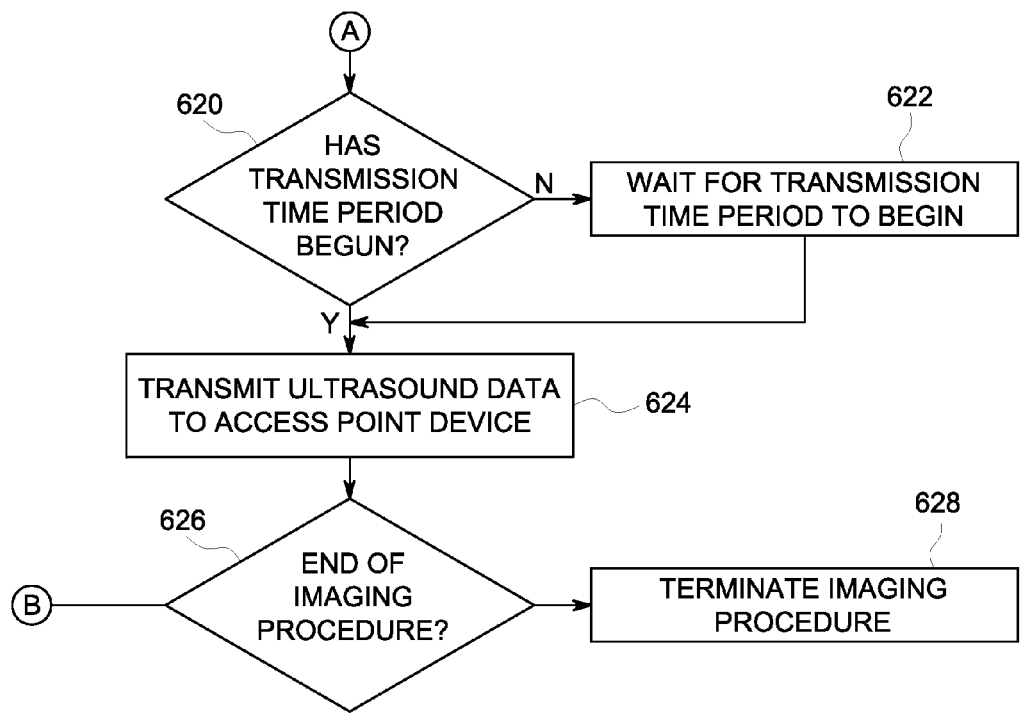

FIGS. 6A and 6B illustrate a flowchart of one embodiment of a method 600 for wireless communication in an ultrasound imaging system. The method 600 may be used in conjunction with an ultrasound imaging system having ultrasound probes that acquire ultrasound data from a body (e.g., a patient or other test subject) and wirelessly transmit the acquired ultrasound data for processing and display to an operator. In one embodiment, the method 600 may be used to provide for wireless communication in the imaging system 100 shown in FIG. 1.

At 602, an ultrasound probe is associated with a body to be imaged. For example, one or more of the probes 104a-f (shown in FIG. 1) may be assigned to different bodies 108a-e (shown in FIG. 1) to concurrently perform imaging procedures on a plurality of the bodies 108a-e. The association between the probes 104 and the bodies 108 may be manually established or may be automatically established. For example, the probes 104 may be automatically assigned to a particular patient by scanning a barcode or other identifying indicia on the probe 104 when the probe 104 is brought into an examination room having the patient in the room.

At 604, a determination is made as to whether multiple probes are imaging the same body during an imaging procedure. For example, two or more probes may be used to acquire ultrasound data from the same patient during the same imaging procedure or time period. This determination may be made by determining if multiple probes are assigned to the same patient. If multiple probes are assigned to the same patient, then the ultrasound pulses emitted by the probes into the patient may interfere with each other. As a result, flow of the method 600 may proceed to 606, where acoustic bandwidth allocation may be performed. On the other hand, if multiple probes are not imaging the same patient during the same time period, or if multiple probes are imaging the same patient but the ultrasound pulses emitted into the patient do not interfere with each other (e.g., are spaced sufficiently far apart), then acoustic bandwidth allocation may be unnecessary.

At 606, acquisition time periods are allocated to the multiple probes imaging the same body. For example, non-overlapping time periods may be assigned to each of the probes imaging the same body. Each probe may only transmit ultrasound pulses into the body during the acquisition time period assigned to the probe in one embodiment. The allocation of acquisition time periods between the probes imaging the same body can reduce or eliminate interference of the ultrasound pulses emitted from one probe with the ultrasound pulses emitted form another probe.

At 608, the probe is logically connected with an access point device. For example, one or more of the probes 104a-f (shown in FIG. 1) may be assigned to one of the access point devices 110a-c (shown in FIG. 1). The probe 104 may be assigned to an access point device 110 based on a proximity of the probe 104 to the access point device 110, a number of other probes 104 assigned to the access point device 110, an amount of available wireless data bandwidth of the access point device 110, and the like.

In another embodiment, the probe may not be assigned or logically connected with an access point device. For example, the probe may not wirelessly transmit acquired ultrasound data as data that is addressed to one of several access point devices and no other access point devices. The probe may wirelessly broadcast the ultrasound data such that the data is not addressed or directed to any particular access point device.

At 610, a determination is made as to whether multiple probes are logically connected with or assigned to the same access point device. For example, two or more probes may be assigned to the same access point device and may attempt to concurrently transmit acquired ultrasound data to the same access point device. If multiple probes are assigned to the same access point device, then the ultrasound data that is wirelessly transmitted from one probe may interfere with the ultrasound data that is wirelessly transmitted to another probe. As a result, wireless bandwidth allocation may be necessary and flow of the method 600 may proceed to 612. Alternatively, if multiple probes are not assigned to the same access point device and/or the amount of available wireless bandwidth is sufficient to handle concurrent transmission from multiple probes, then wireless bandwidth allocation may be unnecessary and flow of the method 600 can proceed to 614.

At 612, transmission time periods are allocated to the multiple probes assigned to the same access point device. For example, non-overlapping time periods may be assigned to each of the probes assigned to a common access point device. Each probe may only transmit ultrasound data to the assigned access point device during the transmission time period assigned to the probe in one embodiment. The allocation of transmission time periods between the probes imaging the same body can reduce or eliminate interference of the ultrasound data that is wirelessly transmitted to the same access point device.

At 614, a determination is made as to whether an acquisition time period has begun for the probe. If the acquisition time period has not begun, then the probe may not be able to begin acquiring ultrasound data from the body. As a result, flow of the method 600 can proceed to 616. On the other hand, if the acquisition time period has begun, then the probe can begin acquiring ultrasound data from the body, such as by transmitting ultrasound pulses into the body. As a result, flow of the method 600 can proceed to 618.

At 616, the probe waits until the acquisition time period allocated to the probe begins. For example, the probe may refrain from transmitting ultrasound pulses into the body until the next acquisition time period allocated to the probe begins. Once the acquisition time period begins, flow of the method 600 may continue to 618.

At 618, ultrasound data is acquired from the body. For example, the probe may transmit ultrasound pulses into the body and receive echoes of the pulses off of the body. The probe may convert the received echoes into electrical signals representative of the echoes. These signals may be referred to as, or include, acquired ultrasound data.

At 620, a determination is made as to whether a transmission time period has begun for the probe. If the transmission time period has not begun, then the probe may not transmit acquired ultrasound data to an access point device. As a result, flow of the method 600 can proceed to 622. On the other hand, if the transmission time period has begun, then the probe can transmit acquired ultrasound data to the access point device, such as by wirelessly transmitting ultrasound data to the access point device. As a result, flow of the method 600 can proceed to 624.

At 622, the probe waits until the transmission time period allocated to the probe begins. For example, the probe may refrain from wirelessly transmitting ultrasound data until the next transmission time period allocated to the probe begins. The probe can continue acquiring ultrasound data and storing the ultrasound data in an internal memory until the next transmission time period begins. Once the transmission time period begins, flow of the method 600 may continue to 624.

At 624, acquired ultrasound data is wirelessly transmitted by the probe to the access point device. For example, the probe may wirelessly transmit ultrasound data that is addressed to one or more of the access point devices. The access point devices receive the ultrasound data and communicate the data to a processing subsystem that processes the data to form one or more ultrasound images.

At 626, a determination is made as to whether the imaging procedure on the body has completed. For example, a determination may be made as to whether sufficient ultrasound data has been obtained to form one or more images or whether an operator of the probe has deactivated or turned off the probe. If the imaging procedure has completed, flow of the method 600 can continue to 628, where the imaging procedure is terminated. On the other hand, if the imaging procedure has not completed, then flow of the method 600 may return to 614 to continue to acquire ultrasound data during acquisition time periods assigned to the probe.

Figure 7:
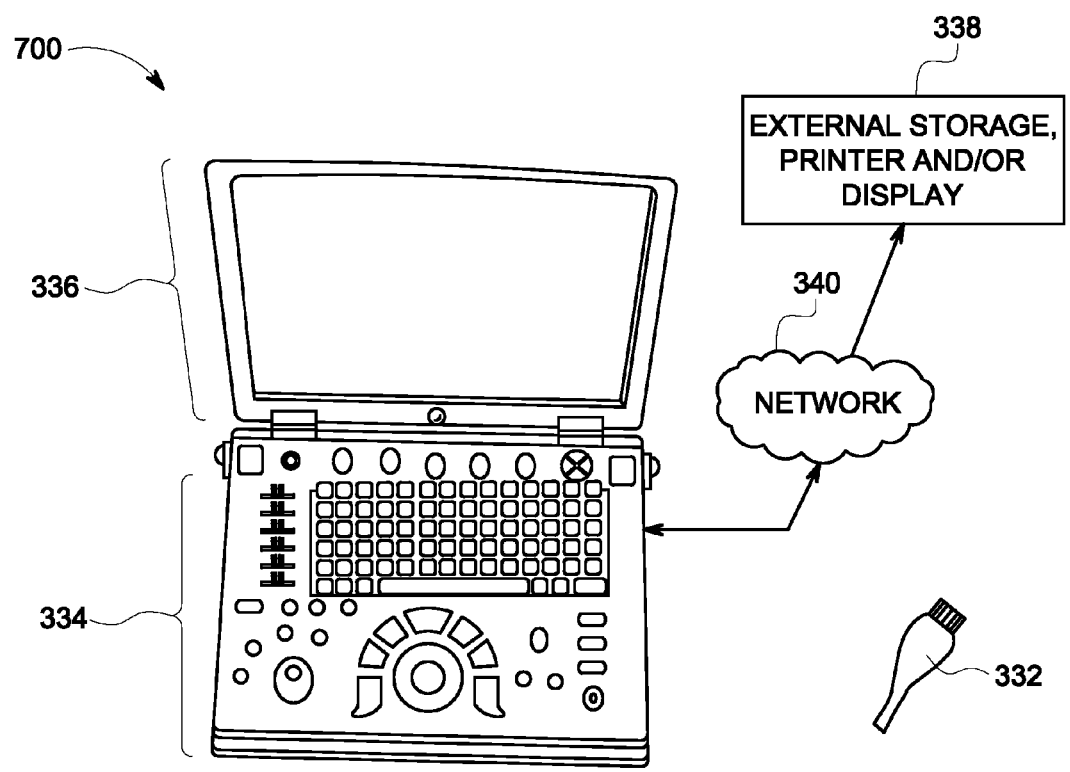
FIG. 7 illustrates a 3D-capable miniaturized ultrasound system.

FIG. 7 illustrates a 3D-capable miniaturized ultrasound system 700 having a probe 332 that may be configured to acquire 3D ultrasonic data or multi-plane ultrasonic data. For example, the probe 332 may have a 2D array of elements 106 as discussed previously with respect to the probe 104 of FIG. 1. The probe 332 may be physically or mechanically disconnected from the system 700. For example, the probe 332 may not be joined with other components of the system 700 by any wires, cables, and the like. The probe 332 may wirelessly transmit acquired ultrasound data to the system 700, as described above. Although not shown in FIG. 7, the system 700 may have an access point device 110 (shown in FIG. 1), such as an antenna disposed inside the system 700.

A user interface 334 (that may also include an integrated display 336) is provided to receive commands from an operator. As used herein, "miniaturized" means that the ultrasound system 330 is a handheld or hand-carried device or is configured to be carried in a person's hand, pocket, briefcase-sized case, or backpack. For example, the ultrasound system 330 may be a hand-carried device having a size of a typical laptop computer. The ultrasound system 330 is easily portable by the operator. The integrated display 336 (e.g., an internal display) is configured to display, for example, one or more medical images.

The ultrasonic data may be sent to an external device 338 via a wired or wireless network 340 (or direct connection, for example, via a serial or parallel cable or USB port). In some embodiments, the external device 338 may be a computer or a workstation having a display, or the DVR of the various embodiments. Alternatively, the external device 338 may be a separate external display or a printer capable of receiving image data from the hand carried ultrasound system 330 and of displaying or printing images that may have greater resolution than the integrated display 336.

Figure 8:
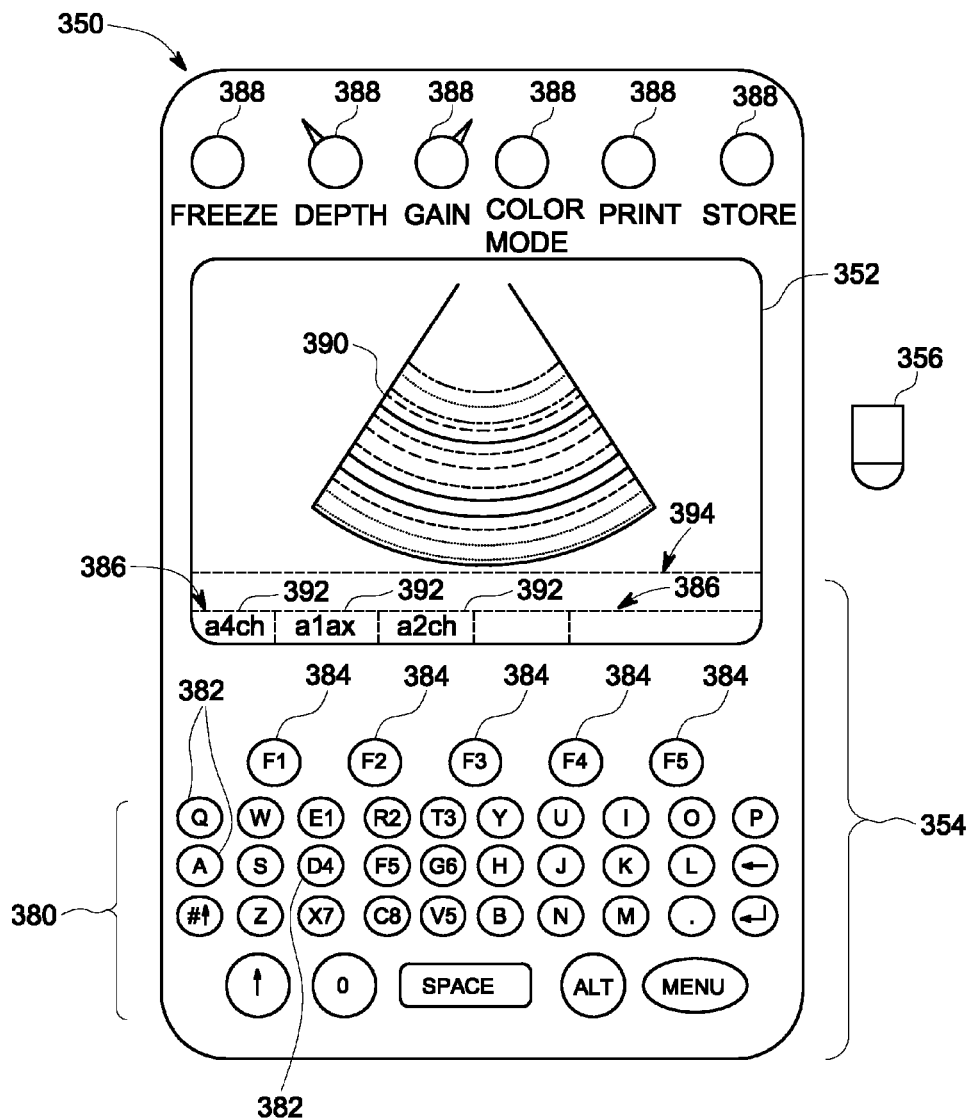
FIG. 8 illustrates a hand carried or pocket-sized ultrasound imaging system.

FIG. 8 illustrates a hand carried or pocket-sized ultrasound imaging system 350 wherein the display 352 and user interface 354 form a single unit. By way of example, the pocket-sized ultrasound imaging system 350 may be a pocket-sized or hand-sized ultrasound system approximately 2 inches wide, approximately 4 inches in length, and approximately 0.5 inches in depth and weighs less than 3 ounces. The pocket-sized ultrasound imaging system 350 generally includes the display 352, user interface 354, which may or may not include a keyboard-type interface and an input/output (I/O) port for connection to a scanning device, for example, an ultrasound probe 356. The display 352 may be, for example, a 320×320 pixel color LCD display (on which a medical image 190 may be displayed). A typewriter-like keyboard 380 of buttons 382 may optionally be included in the user interface 354.

The probe 356 may be physically or mechanically disconnected from the system 350. For example, the probe 356 may not be joined with other components of the system 350 by any wires, cables, and the like. The probe 356 may wirelessly transmit acquired ultrasound data to the system 350, as described above. Although not shown in FIG. 8, the system 350 may have an access point device 110 (shown in FIG. 1), such as an antenna disposed inside the system 700.

Multi-function controls 384 may each be assigned functions in accordance with the mode of system operation (e.g., displaying different views). Therefore, each of the multi-function controls 384 may be configured to provide a plurality of different actions. Label display areas 386 associated with the multi-function controls 384 may be included as necessary on the display 352. The system 350 may also have additional keys and/or controls 388 for special purpose functions, which may include, but are not limited to "freeze," "depth control," "gain control," "color-mode," "print," and "store."

One or more of the label display areas 386 may include labels 392 to indicate the view being displayed or allow a user to select a different view of the imaged object to display. The selection of different views also may be provided through the associated multi-function control 384. The display 352 may also have a textual display area 394 for displaying information relating to the displayed image view (e.g., a label associated with the displayed image).

It should be noted that the various embodiments may be implemented in connection with miniaturized or small-sized ultrasound systems having different dimensions, weights, and power consumption. For example, the pocket-sized ultrasound imaging system 350 and the miniaturized ultrasound system 700 may provide the same scanning and processing functionality as the system 100 (shown in FIG. 1)

Figure 9:
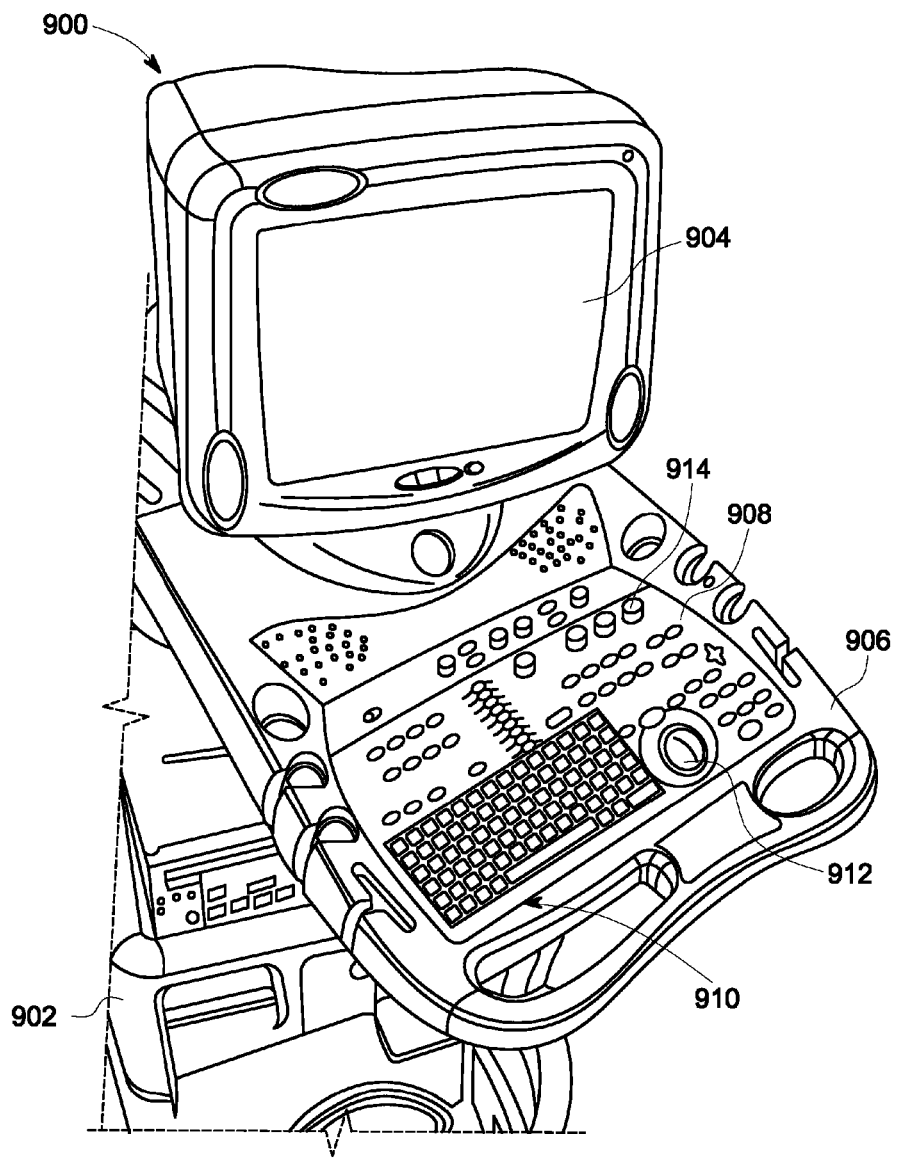
FIG. 9 illustrates an ultrasound imaging system provided on a movable base.

FIG. 9 illustrates an ultrasound imaging system 900 provided on a movable base 902. The portable ultrasound imaging system 900 may also be referred to as a cart-based system. A display 904 and user interface 906 are provided and it should be understood that the display 904 may be separate or separable from the user interface 906. The user interface 906 may optionally be a touchscreen, allowing the operator to select options by touching displayed graphics, icons, and the like.

The user interface 906 also includes control buttons 908 that may be used to control the portable ultrasound imaging system 900 as desired or needed, and/or as typically provided. The user interface 906 provides multiple interface options that the user may physically manipulate to interact with ultrasound data and other data that may be displayed, as well as to input information and set and change scanning parameters and viewing angles, etc. For example, a keyboard 910, trackball 912 and/or multi-function controls 914 may be provided.

One or more probes (such as the probes 104 shown in FIG. 1) may be communicatively coupled with the system 900 to wirelessly transmit acquired ultrasound data to the system 900, as described above in connection with the system 100 shown in FIG. 1.

The various embodiments and/or components, for example, the modules, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a floppy disk drive, optical disk drive, and the like. The storage device may also be other similar means for loading computer programs or other instructions into the computer or processor.

As used herein, the term "computer" or "module" may include any processor-based or microprocessor-based system including systems using microcontrollers, reduced instruction set computers (RISC), application specific integrated circuits (ASICs), logic circuits, and any other circuit or processor capable of executing the functions described herein. The above examples are exemplary only, and are thus not intended to limit in any way the definition and/or meaning of the term "computer".

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments of the subject matter described herein. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to user commands, or in response to results of previous processing, or in response to a request made by another processing machine.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments of the described subject matter without departing from their scope. While the dimensions and types of materials described herein are intended to define the parameters of the various embodiments of the invention, the embodiments are by no means limiting and are exemplary embodiments. Many other embodiments will be apparent to one of ordinary skill in the art upon reviewing the above description. The scope of the various embodiments of the inventive subject matter should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose the various embodiments of the invention, including the best mode, and also to enable one of ordinary skill in the art to practice the various embodiments of the invention, including making and using any devices or systems and performing any incorporated methods. The patentable scope of the various embodiments of the invention is defined by the claims, and may include other examples that occur to those skilled in the art. Such other examples are intended to be within the scope of the claims if the examples have structural elements that do not differ from the literal language of the claims, or if the examples include equivalent structural elements with insubstantial differences from the literal languages of the claims.

What is claimed is:

1. A wireless ultrasound imaging system comprising:
   plurality of probes each having at least one transducer element configured to emit ultrasound pulses into one or more regions of interest and receive echoes of the pulses, the probes configured to generate and concurrently acquire ultrasound data based on the echoes and to wirelessly transmit the ultrasound data;
   at least one access point device having one or more antennas and configured to wirelessly receive the ultrasound data concurrently from the probes; and
   a processing subsystem having one or more processors and communicatively coupled with the at least one access point device, the processing subsystem receiving the ultrasound data from the probes and creating one or more images based on the ultrasound data, wherein the processing subsystem is configured to allocate different transmission time periods to the plurality of probes based on a number of the plurality of probes broadcasting ultrasound data such that a first probe is transmitting to the at least one access point at a first transmission time period and a second probe is transmitting to the at least one access point at a second transmission time period.

2. The wireless ultrasound imaging system of claim 1, wherein the probes are configured to acquire ultrasound data when not wirelessly transmitting to the at least one access point device.

3. The wireless ultrasound imaging system of claim 1, wherein the plurality of the probes are configured to concurrently acquire different sets of the ultrasound data from two or more different regions of interest and wirelessly transmit the different sets of the ultrasound data to the processing subsystem.

4. The wireless ultrasound imaging system of claim 1, wherein the plurality of the probes are configured to acquire different sets of the ultrasound data from a common region of interest during a common imaging procedure.

5. The wireless ultrasound imaging system of claim 1, wherein the processing subsystem is configured to allocate different acquisition time periods among a plurality of the probes, the processing subsystem is configured to communicate the different acquisition time periods to the probes and the probes emitting the ultrasound pulses during the acquisition time periods allocated to the probes.

6. The wireless ultrasound imaging system of claim 5, wherein the processing subsystem is further configured to vary at least one of a sequence of the acquisition time periods or a length of one or more of the acquisition time periods among the acquisition time periods that are allocated to different probes.

7. The wireless ultrasound imaging system of claim 5, wherein at least one of the acquisition time periods is based on one or more of a frame rate at which the ultrasound pulses are emitted by one or more of the probes, a type of the ultrasound images based on the data obtained by one or more of the probes, a category of the region of interest being imaged by one or more of the probes, or a number of the probes that are acquiring ultrasound data from a common region of interest during the same acquisition time period.

8. The wireless ultrasound imaging system of claim 1, wherein the processing subsystem is configured to assign the first and second probe to a first channel such that the first and second probe wirelessly transmit the ultrasound data to the at least one access point device along the first channel.

9. The wireless ultrasound imaging system of claim 8, wherein the processing subsystem is configured to vary at least one of a sequence of the transmission time periods or a length of one or more of the transmission time periods among the transmission time periods that are allocated to different probes.

10. The wireless ultrasound imaging system of claim 8, wherein the probes include an internal memory configured to store the ultrasound data until the probes transmit the ultrasound data during the allocated transmission time periods.

11. The wireless ultrasound imaging system of claim 1, wherein the processing subsystem is configured to allocate different acquisition time periods among the plurality of the probes, further comprising a user interface that receives input from an operator to manually adjust one or more of the acquisition time periods or the transmission time periods.

12. A method for wireless communication in an ultrasound imaging system, the method comprising:
    directing plural probes to concurrently acquire ultrasound data by emitting ultrasound pulses into two or more imaged bodies and receive echoes of the pulses;
    directing the probes to wirelessly transmit the ultrasound data during different transmission time periods, wherein the different transmission time periods are allocated among the probes based on a number of the probes broadcasting ultrasound data, such that a first probe is transmitting to the at least one access point at a first transmission time period and a second probe is transmitting to the at least one access point at a second transmission time period;
    wirelessly receiving the ultrasound data from the probes at one or more access point devices; and
    processing the ultrasound data at an ultrasound processing subsystem that is communicatively coupled with the one or more access point devices to form one or more images.

13. The method of claim 12, further comprising directing the probes to acquire ultrasound data when not wirelessly transmitting to the one or more access point devices.

14. The method of claim 12, wherein at least two probes wirelessly transmit the ultrasound data concurrently to at least one access point.

15. The method of claim 12, wherein directing the probes to concurrently acquire the ultrasound data includes allocating different acquisition time periods among a plurality of the probes and directing the probes to emit the ultrasound pulses into the body during the acquisition time periods allocated to the probes.

16. A computer readable non-transitory storage medium for a wireless ultrasound imaging system having a processor and plural probes configured to generate ultrasound data by emitting ultrasound pulses into two or more imaged bodies and receiving echoes of the pulses, the computer readable storage medium include instructions to command the processor to:

direct a plurality of the probes to concurrently acquire the ultrasound data;

direct the probes to wirelessly transmit the ultrasound data during different transmission time periods, wherein the different transmission time periods are allocated among the probes based on a number of the probes broadcasting ultrasound data, such that a first probe is transmitting to the at least one access point at a first transmission time period and a second probe is transmitting to the at least one access point at a second transmission time period;

wirelessly receive the ultrasound data from the probes at one or more access point devices; and direct the imaging system to process the ultrasound data at an ultrasound processing subsystem that is communicatively coupled with the one or more access point devices to form one or more images.

17. The computer readable non-transitory storage medium of claim 16, further comprising directing the probes to acquire ultrasound data when not wirelessly transmitting to at least one access point device.

18. The computer readable non-transitory storage medium of claim 16, wherein the probes wirelessly transmit the ultrasound data concurrently to at least one access point.

19. The computer readable non-transitory storage medium of claim 16, wherein the instructions command the processor to allocate different acquisition time periods among a plurality of the probes and direct the probes to emit the ultrasound pulses into the body during the acquisition time periods allocated to the probes.

* * * * *